(12) United States Patent
Zweig

(10) Patent No.: US 6,984,307 B2
(45) Date of Patent: Jan. 10, 2006

(54) DUAL GLUCOSE-HYDROXYBUTYRATE ANALYTICAL SENSORS

(76) Inventor: Stephen Eliot Zweig, 224 Vista de Sierra, Los Gatos, CA (US) 95030

( * ) Notice: Subject to any disclaimer, the term of this patent is extended or adjusted under 35 U.S.C. 154(b) by 530 days.

(21) Appl. No.: 10/264,206

(22) Filed: Oct. 3, 2002

(65) Prior Publication Data

US 2003/0068666 A1 Apr. 10, 2003

Related U.S. Application Data

(60) Provisional application No. 60/327,535, filed on Oct. 5, 2001.

(51) Int. Cl.
*G01N 27/327* (2006.01)
*G01N 21/00* (2006.01)

(52) U.S. Cl. ............... 205/777.5; 436/164; 422/56; 204/403.04; 204/403.1; 204/403.11; 204/403.14

(58) Field of Classification Search ............... 204/403.01–403.12, 403.14, 403.15; 436/14, 436/95, 128, 164; 422/56; 205/777.5
See application file for complete search history.

(56) References Cited

U.S. PATENT DOCUMENTS

| | | | |
|---|---|---|---|
| 3,814,668 A | 6/1974 | Blake et al. | |
| 4,147,514 A | 4/1979 | Magers et al. | |
| 4,225,410 A | 9/1980 | Pace | |
| 4,397,956 A | 8/1983 | Maggio | |
| 4,545,382 A | 10/1985 | Higgins et al. | |
| 4,548,907 A | 10/1985 | Seitz et al. | |
| 4,682,895 A | 7/1987 | Costello | |
| 5,049,487 A | 9/1991 | Phillips et al. | |
| 5,126,275 A * | 6/1992 | Hatch et al. | 436/169 |
| 5,139,685 A | 8/1992 | de Castro et al. | |
| 5,344,754 A | 9/1994 | Zweig | |
| 5,597,532 A * | 1/1997 | Connolly | 422/58 |
| 5,628,890 A * | 5/1997 | Carter et al. | 204/403.05 |
| 5,695,949 A | 12/1997 | Galen et al. | |
| 5,708,247 A | 1/1998 | McAleer et al. | |
| 5,843,692 A | 12/1998 | Phillips et al. | |
| 5,951,836 A | 9/1999 | McAleer et al. | |
| 5,968,836 A | 10/1999 | Matzinger et al. | |
| 6,027,692 A | 2/2000 | Galen et al. | |
| 6,090,251 A | 7/2000 | Sundberg et al. | |
| 6,143,164 A | 11/2000 | Heller et al. | |
| 6,231,920 B1 | 5/2001 | Guadalupe et al. | |
| 6,277,641 B1 * | 8/2001 | Yager | 436/52 |

FOREIGN PATENT DOCUMENTS

EP 1113263 A2 * 7/2001
WO WO 9958709 A1 * 11/1999

OTHER PUBLICATIONS

Batchelor et. al. "Ampherometric assay for the Ketone body 3-hydroxybutyrate" Analytica Chimica Acta 221 (1989) 289-294.
Cunningham "Introduction to Bioanalytical Sensors" Wiley Interscience (1998) 207-259.

* cited by examiner

*Primary Examiner*—Alex Noguerola

(57) ABSTRACT

Diagnostic dry reagent tests capable of reacting with a single drop of whole blood and reporting both glucose and beta-hydroxybutyrate levels are taught. Such dry reagent tests may employ electrochemical detection methodologies, optical detection methodologies, or both methodologies. These tests help facilitate the early detection of the onset of ketoacidosis in diabetes.

23 Claims, 5 Drawing Sheets

DUAL GLUCOSE-HYDROXYBUTYRATE ANALYTICAL SENSORS

BACKGROUND OF THE INVENTION

1. Field of the Invention

The field of the invention is improved dry reagents for instrumented whole blood tests useful for diabetics.

2. Description of the Related Art

This application claims the priority benefit of provisional patent application No. 60/327,535 "Dual glucose-hydroxybutyrate analytical sensors", filed Oct. 5, 2001.

Blood glucose monitoring has revolutionized the treatment of diabetes. Large-scale clinical trials have clearly demonstrated that frequent blood glucose monitoring can aid in the prevention of many of the long-term complications of diabetes, such as diabetic retinopathy, circulatory disorders, and death. After nearly twenty years of development, blood glucose monitoring has now become a several billion dollar a year business.

As the blood glucose-monitoring field has advanced, the various blood glucose monitors have become more and more generic. All possess good accuracy, ease of use, and speed. As a result, the various manufacturers of blood glucose monitors have focused major efforts on gaining minor technical advantages to make minor improvements in their respective market shares. Such improvements may include minor improvements in speed, blood sample size, ease of sample application, cost, etc. All, however, produce test strips that measure only blood glucose.

Although blood glucose is clearly the most important biochemical parameter to measure in diabetes, it is not the only parameter of medical interest. Other parameters of medical relevance include glycosylated hemoglobin, used to measure long-term blood glucose control, and ketone levels, used to indicate if the patient is at risk for diabetic ketoacidosis.

Diabetic ketoacidosis is a major complication of diabetes. Such conditions occur during times of extreme insulin deficiency. Here the diabetic's tissues are unable to process glucose, and as a result, initiate the biochemical processes that result in the formation of ketones and excess blood glucose. During periods of insulin starvation, body cells are unable to metabolize glucose as an energy source and instead metabolize fat as an energy source. Ketone bodies, made up of acectoacetate, acetone, and beta-hydroxybutyrate (also called D-3-hydoxybutyrate) are produced from this fat metabolism process, and these build up in the blood. Excessive levels of ketone bodies in turn can alter the pH balance of the blood to a more acidic state, as well as other undesirable complications, eventually leading to confusion, coma, and death. In the early stages of fat metabolism, the ketone bodies contain relatively large amounts of acectoacetate and acetone. However in more profound ketoacidosis, the ketone bodies contain primarily beta-hydroxybutyrate.

Each year, about 12 out of every 1000 diabetics are hospitalized for Ketoacidosis, and 2% of those hospitalized die from it. It is the commonest cause of death for diabetic children.

Early detection is the best way to prevent diabetic ketoacidosis. If detected in time, rehydration and low-dose insulin therapy can be used to treat ketoacidosis. Thus means to ensure that the onset of ketoacidosis is promptly detected are of extreme utility to diabetics.

Means to measure ketone levels are known in the art. These include visually read test strips for acetone or acectoacetate in the urine, as well as whole blood tests for beta-hydroxybutyrate. Diabetics are trained that whenever their glucose levels are high, they should follow up by immediately running a separate ketone test.

Examples of urine ketone dry reagent tests include Keto-stix, Keto-Diastix (Beyer) or Chemstrip K (Roche). Such urinary tests generally use non-enzymatic detection methods (such as nitroprusside based chemistries) that are primarily sensitive to acectoacetate, slightly sensitive to acetone, and not at all sensitive to beta-hydroxybutyrate. One drawback of tests that measure only urinary acectoacetate or acetone is that such tests can miss or underreport extreme levels of ketoacidosis. In mild ketosis, the body produces acectoacetate, acetone and beta-hydroxybutyrate in relatively proportionate amounts, and thus urinary tests for acectoacetate and acetone will detect mild ketosis. However in extreme ketoacidosis, the body produces mostly beta-hydroxybutyrate and relatively small amounts of acectoacetate and acetone. Thus non-enzymatic nitroprusside based acectoacetate and acetone sensitive tests may become insensitive to extreme ketoacidosis right when they are needed the most.

Simple dry reagent whole blood tests for beta-hydroxybutyrate, the most clinically relevant indicator of ketoacidosis, are known in the art. Presently, such dry reagent tests use a disposable reagent that performs only the beta-hydroxybutyrate test. Often this disposable beta-hydroxybutyrate reagent is read in a meter that is capable of reading a number of different types of single test reagents. For example, GDS diagnostics, Elkhart Ind., sells the "Stat-Site™" meter, which can read separate colorimetric dry reagent tests for either whole blood glucose or ketones (beta-hydroxybutyrate). This technology is taught in U.S. Pat. No. 5,139,685. Polymer Technology Systems of Indianapolis Ind. sells the Bioscanner™ meter that can also read separate calorimetric dry reagent tests for either whole blood glucose or ketones. Similarly, MediSense sells the "Precision Xtra™" meter that can read separate electrochemical dry reagent tests for either glucose or beta-hydroxybutyrate.

Other one-meter-multiple-reagents systems are in commercial use. The LXN Corporation sells the Duet™ and "In Charge System™" meters that are capable of reading either a calorimetric glucose dry reagent test, or alternatively a calorimetric glycated protein (fructosamine) dry reagent test. These are discussed in more detail in U.S. Pat. Nos. 5,695,949 and 6,027,692.

Although diabetics are accustomed to testing their blood glucose several times a day, they may often forget to run a ketone test, since such tests require extra reagents and effort. Indeed, in an effort to correct for this normal human lapse, some glucose meters, such as the LifeScan "ultra" blood glucose system, will attempt to remind users to run ketone tests by an extra "Ketones?" meter prompt. However, clearly many diabetics will ignore this reminder.

Ideally, what is best from a medical perspective is a blood glucose test that automatically (without any extra user thought, process, or intervention) also reports blood beta-hydroxybutyrate levels using the same drop of blood used to perform the standard and habitual glucose test. Indeed such a combined test would save many lives by facilitating the early detection of ketoacidosis. Additionally, such combined tests would be of strong commercial interest as well, since if everything else were equal, a combined glucose/beta-hydroxybutyrate test would be strongly preferred by diabetics over the glucose-only tests presently used.

However no such single blood drop activated, combined blood-glucose/blood-beta-hydroxybutyrate dry reagent has previously been proposed, invented, or commercialized.

By contrast, combined glucose—ketone test strips have been available for urine testing for many years. Given the competitive nature of the blood glucose-monitoring field, why does this discrepancy exist between the long-term commercialization of combined urine glucose-ketone dry reagent test strips, and the complete lack of any prior art in combined whole blood glucose/beta-hydroxybutyrate dry reagent tests?

The difference is almost certainly due to the radically different nature of the two different sample types. Urine is available in large (100+ milliliter [ml]) quantities. It is nearly transparent. Thus a combined glucose—ketone dry regent test may be made by simply putting a calorimetric glucose dry reagent test pad onto solid support a certain distance away from a colorimetric ketone dry regent test pad. Because large amounts of sample are present, the distance between the two test pads can be so great as to minimize any "cross talk" due to reaction intermediate or colorimetric dye indicator diffusion between the two pads.

It is often the case in nearly every area of technology that devices optimized for a single purpose outperform devices optimized for multiple purposes. Blood glucose testing has been a mature field for nearly twenty years, and blood glucose meters and reagents have evolved to a highly advanced state. Patients and physicians are unlikely to accept a dual glucose—beta-hydroxybutyrate reagent as being a genuine improvement unless, at a minimum, the glucose portion of the reagent performs at a level that is competitive with stand-alone blood glucose tests. If the combined reagent requires no extra user effort, the blood glucose portion is competitive, and the extra cost for the secondary function is minor, then the user will benefit and the combined reagent will likely be a medical and commercial success.

In this context, the commercial success of combined urine—ketone test strips can be understood. These devices function with the same urine sample and require no additional user effort. The urine blood glucose part of a combined urinary glucose-ketone test strip performs as well as stand-alone urine blood glucose test strip.

By contrast, combined whole blood glucose—beta-hydroxybutyrate dry reagents must overcome some formidable technical challenges. Whereas urine samples typically have a volume of 100 ml (milliliters), blood samples, typically derived from a fingerstick, are more typically have a volume around 1–10 ul, (microliters). This is nearly five orders of magnitude less in size. Whereas urine is nearly transparent and relatively free of optical and electrochemical interfering substances, blood is intensely colored and contains nearly 50% hemoglobin and other strong optical and electrochemical interfering substances.

In order to meet the requirement for no additional user effort, a whole blood combined glucose—ketone/beta-hydroxybutyrate test must place both the glucose sensing means and the ketone/beta-hydroxybutyrate sensing means close enough together as to both be activated with the same small (1–10 ul) drop of whole blood. Further, the test must be designed to minimize "cross talk" between such closely spaced sensing means.

3. Prior Art

Visually read beta-hydroxybutyrate sensors and ketone sensors.

U.S. Pat. No. 4,147,514 teaches a urine test strip for detecting urinary acetone and acetoacetic acid by means of an improved nitroprusside reaction. This urinary ketone test strip patent, in conjunction with U.S. Pat. No. 3,814,668 for a urinary glucose test strip, forms the basis for the popular Keto-Diastix® Reagent strips for urinalysis, produced by Bayer Corporation, Elkhart Ind.

U.S. Pat. No. 4,397,956 teaches a whole-blood modification of the combined urine glucose—non-enzymatic ketone test strip. In this modification, a separate glucose reagent pad and separate ketone pad are mounted on the same support. Both pads are covered with a blood separation coating. Two drops of blood, one for each separate reagent pad, are applied to the device. The user manually times the reaction by allowing the blood to soak in for one minute, and then manually wipes or washes off the excess blood from the outer layer of the pad.

As taught, the device of U.S. Pat. No. 4,397,956 measures whole blood acetoacetate using the sodium nitroprusside reaction, rather than the preferred enzymatic beta-hydroxybutyrate specific reaction. Thus the test reagent of U.S. Pat. No. 4,397,956 would be expected to suffer from the previously mentioned beta-hydroxybutyrate insensitivity clinical deficiencies of this type of reaction chemistry. This clinical deficiency, on top of other test deficiencies such as the requirement for multiple blood sample application steps, and extensive user intervention (timing, washing) teaches against the need for a competitive and automated dual glucose/beta-hydroxybutyrate whole blood test.

Prior art for single analyte glucose electrochemical sensors can be found a variety of patents, including many assigned to Genetics International, Medisense, E. Heller, & Company, Therasense, Selfcare, Boehringer Mannheim, and others. These include U.S. Pat. Nos. 4,545,382; 4,711,245; 4,758,323; 5,262,035; 5,262,305; 5,264,105; 5,286,362; 5,312,590; 5,320,725; 5,509,410; 5,628,890; 5,682,884; 5,708,247; 5,727,548; 5,820,551; 5,951,836; 6,134,461 and 6,143,164;

Prior art for single analyte hydroxybutyrate electrochemical sensors was published by Batchelor, et. al, "Amphorometric assay for the ketone body 3-hydroxybutyrate" Analytica Chimica Acta 221 (1989), 289–294.

U.S. Pat. No. 4,225,410 discloses an integrated array of electrochemical sensors where each sensor is a complete self-contained electrically isolated electrochemical cell, mounted on a solid support that contains a plurality of such cells. As is the case for previous art covering multiple colorimetric reagent pads on a single solid phase support, placing multiple electrically isolated electrochemical cells on a single solid phase support is also unsuitable for small rapid, low cost, analysis of 1–10 ul volume whole blood samples. Due to the surface tension characteristics of blood, separation of a single 1–10 ul droplet of whole blood into multiple electrically isolated droplets must overcome surface tension effects, and thus is energetically unfeasible without the intervention of energy added by some extra mechanisms. Although such mechanisms are known in the art (e.g. U.S. Pat. No. 6,090,251, etc.), the extreme manufacturing cost sensitivity of practical blood glucose tests should be recognized. Any commercially practical dual-purpose glucose—beta-hydroxybutyrate electrochemical sensor must be price competitive with mass marketed single purpose glucose sensors, which can typically be produced at costs of about 10–20 cents per sensor. This brutal economic constraint on manufacturing costs eliminates all but the simplest combined designs from consideration. At the present state-of-the art, it appears unlikely that means will be found to mass produce, for a total cost of 10 to 20 cents per unit, a fully functional combined purpose electrode-containing-reagent, that also contains extra mechanisms to reliably and almost instantly separate a microlitre sized drop of blood into two or more electrically isolated droplets.

Prior art for electrically triggered optical test reagents includes U.S. Pat. Nos. 5,344,754 and 5,554,531.

Prior art for fiber optical biochemical sensors includes U.S. Pat. No. 4,682,895, which teaches fiber optical probes with sharp, 180 degree bends at the sensor tip. Other prior art includes U.S. Pat. No. 4,548,907, which teaches bifurcated optical probes for use with pH dependent fluorophores.

SUMMARY OF THE INVENTION

The two major detection methods employed in modern dry reagent blood glucose tests are calorimetric (best exemplified by the LifeScan "One-Touch" and "SureStep" systems), and electrochemical (best exemplified by the Medisense "Precision" family of systems. All work with extremely small sample sizes, typically under 10 ul, all are "automatic" in the sense that after the addition of a single drop of blood, all further analysis and data reporting is done automatically by the meter. These systems set the standard for performance that a successful combined glucose/beta-hydroxybutyrate reagent must match or exceed.

In this disclosure, reagents, systems and methods to add additional whole-blood beta-hydroxybutyrate detection and reporting means to novel and state-of-the-art blood glucose reagents are disclosed. Such systems and methods disclosed herein are designed to enable the combined test to have performance characteristics similar to modern dedicated single-purpose blood glucose reagents.

According to this invention, the main principle that applies throughout is that both sensors in the combined reagent device should be held so close together that both can be simultaneously rehydrated and activated using a single, unseparated, whole blood drop. Because the two sensors are so close together, however, the system must also be designed to minimize "cross-talk" between the two different neighboring sensors.

Enzymatic detection schemes: To briefly review, glucose and beta-hydroxybutyrate can be detected using a variety of different enzymatic schemes.

Glucose reacts with the enzyme glucose oxidase. In an electrochemical system, the electrons will then transfer to an electron transfer mediator molecule, such as ferrocine, and then enter the reagent's electrode. In an optical system, glucose oxidase will produce hydrogen peroxide. This in turn will react with a second enzyme, peroxidase, and an indicator dye molecule, such as a benzidine dye.

Alternatively, Glucose may react with a dehydrogenase enzyme, such as hexokinase/glucose-6-phosphate dehydrogenase. This will convert NAD to NADH. In an electrochemical test, the NADH in turn will undergo electron exchange with an electron transfer mediator molecule, such as 4-methyl-o-quinone. This in turn transfers electrons to the reagent's electrode. In an optical system, the NADH will in turn react with the enzyme diaphorase and an optical indicator molecule such as a tetrazolium dye like INT (2-(4-iodophenyl)-3-(4-nitrophenyl)-5-phenyl tetrazolium chloride).

Similarly, beta-hydroxybutyrate reacts with the enzyme beta-hydroxybutyrate dehydrogenase (E.C. 1.1.1.30). This will then convert NAD to NADH. In an electrochemical test, the NADH in turn will undergo electron exchange with an electron transfer mediator molecule, such as 4-methyl-o-quinone. This in turn transfers electrons to the reagent's electrode. In an optical system, the NADH will in turn react with the enzyme diaphorase and an optical indicator molecule such as a tetrazolium dye like INT (2-(4-iodophenyl)-3-(4-nitrophenyl)-5-phenyl tetrazolium chloride).

A more detailed review of these various methods may be found in: "Introduction to Bioanalytical Sensors" by A. Cunningham, published by John Wiley & Sons, 1998, the contents of which are incorporated herein by reference.

Correcting for cross talk effects: In the case of electrochemical tests, avoidance of cross talk between adjacent electrodes requires that the electrochemistry of the glucose portion of the test, which typically may produce larger quantities of electrochemically active reaction intermediates, be properly meshed with the beta-hydroxybutyrate portion of the test, which typically will produce smaller quantities of the electrochemically active reaction intermediates. Here, it is helpful to employ a reference electrode structure that is equally oriented with respect to both sensor electrodes, use reaction chemistries that keep voltage potentials low to minimize side reactions, and employ mathematical deconvolution schemes to correct the typically smaller beta-hydroxybutyrate electrochemical signal for aberrations induced by the typically larger glucose electrochemical signal. Here, the differences in reaction kinetics between the two substrates can also be usefully employed, because the glucose signal will typically develop more quickly than the beta-hydroxybutyrate signal. Thus if at time (early)

$$\text{Signal(glucose channel)} = a1^*[\text{glucose}] + b1^*[\text{beta-hydroxybutyrate}]$$

$$\text{Signal(beta-hydroxybutyrate channel)} = c1^*[\text{glucose}] + d1[\text{beta-hydroxybutyrate}]$$

And at time (later)

$$\text{Signal(glucose channel)} = a2^*[\text{glucose}] + b2^*[\text{beta-hydroxybutyrate}]$$

$$\text{Signal(beta-hydroxybutyrate channel)} = c2^*[\text{glucose}] + b2[\text{beta-hydroxybutyrate}]$$

Then since coefficients [a1 . . . d1], [a2 . . . b2] can be determined in advance for the particular reagent lot, and be loaded into the meter's microprocessor, the simultaneous equations can be solved (often by empirically determined equations and look up tables optimized for that particular reagent/meter system), and the distorting effects of high glucose signals on the fainter beta-hydroxybutyrate signal can be largely overcome.

In the case for an optically based combined test, similar challenges of adequate hydration of the dual sample chemistries, while avoiding cross talk, also exist. In the case of a colorimetric test, cross talk between two different indicator dyes, even with significantly different spectral characteristics, is often an issue because the spectral absorbance of indicator dyes is usually relatively wide. Narrower spectra fluorescent or luminescent detection systems can solve this problem, but at the present state-of-the-art, such solutions tend to be less favored because of increased meter costs.

An additional cross-talk problem occurs if the glucose portion of the test chemistry employs glucose oxidase and hydrogen peroxide generation, and if the beta-hydroxybutyrate portion of the test chemistry employs beta-hydroxybutyrate dehydrogenase and conversion of NAD (nicitonamide adenine dinucleotide) to NADH, and the test geometry is such that the two reaction intermediates can diffuse and intermingle. These issues of cross talk between reagents can occur because the powerful oxidizing effects of hydrogen peroxide upon the NAD-NADH chemistry can distort the beta-hydroxybutyrate reaction. If the glucose portion of the test chemistry employs glucose dehydrogenase or hexokinase, the distortion can be even worse because both the glucose and the beta-hydroxybutyrate reactions will be generating the same signal—NADH.

For these reasons, it is important that the various enzymatic systems be separated from each other, at least to the point where there is minimal diffusion of hydrogen peroxide or NADH between the different reaction centers. This separation can be done by a variety of means, including isolation of the two reagents to different microparticles, reaction beads, etc. For optical tests, one of the simplest means to achieve separation of reaction intermediates, while still permitting both reaction chemistries to be activated by a single blood drop, is to place both reaction chemistry zones onto adjacent portions on the same contiguous piece of absorbent membrane. In this way, a single blood drop can diffuse quickly by capillary movement into both reaction zones. Once the membrane reaction zones are saturated by sample, however, further movement of reaction intermediates occurs only by diffusion, which is considerably slower. Over the time course of a typical glucose or beta-hyroxybutyrate reaction (typically less than one minute), this will typically be only a fraction of a millimeter.

Thus for each type of test methodology, electrochemical or optical, a combined functional reagent must be designed to promote rapid access of a small (typically 10 ul or less) sample of whole blood to two different test chemistries, and also must be designed to minimize cross-talk between the different test chemistries. To the extent that some cross-talk still persists, the meter that reads the reagent may be designed in a way to facilitate the collection of sufficient data, and have sufficient onboard computing means, to do further analysis and mathematical deconvolution in order to accurately separate the two different signals.

DETAILED DESCRIPTION OF THE INVENTION

EXAMPLE 1

Combined "Sandwich" Electrochemical Glucose, b-hydroxybutyrate Sensor with Glucose and Beta-hydroxybutyrate Electrode on a First Surface, and a Single Reference Electrode on a Second Surface The "sandwich" design has certain advantages from the user interface perspective. This design acts to "sip" a small drop of blood into an interior cavity formed by the various layers. This aids to partially protect the sample from the outside environment during the reaction.

Although in examples 1 and 2 given here, glucose oxidase type electrodes are illustrated, it should be understood that the principles taught herein would apply to glucose dehydrogenase type electrodes as well.

Methods:

NADH specific graphite paste C70902D2, Hydrogen peroxide specific graphite paste C40511D8, Silver-Carbon Screen printing paste C70709D14, and reference electrode silver-silver chloride polymer paste C61003D7 may be obtained from Gwent Electronic Materials Ltd., Pontypool, UK. D3-Hydroxybutyrate dehydrogenase may be obtained from Roche molecular chemicals. Glucose oxidase (49180 *Aspergillus niger*) may be obtained from Sigma-Aldrich Corporation.

The NADH specific carbon graphite paste is a mixture of graphite powder, binding agents, and one or more NADH optimized electron transfer agents. Such agents, such as 4-methyl-o-quinone, Meldolas Blue, and the like, work well for dehydrogenase enzymes such as D-3-hydroxybutyrate. Electrochemical tests employing this type of chemistry have been taught by Batchelor et. al., (Analytica Chimica Acta 221 (1989), 289–294). Pure graphite powder suitable for custom formulations may be obtained from Fisher Scientific (Grade 38 graphite powder).

The hydrogen peroxide specific carbon graphite paste is a mixture of graphite powder, binding agents (wax, paraffin oil, poly-chlorotrifluoroethylene etc.), and one or more hydrogen peroxide optimized electron transfer agents. Such agents, such as ferrocine (Alfa chemicals) and the like, work well for oxidase enzymes such as glucose oxidase. Prior art for such electrochemical glucose tests was discussed previously.

The reference silver/silver-chloride paste may be made from a mixture of fine (roughly 10 micron sized) silver and silver-chloride particles present in a roughly 60% silver, 40% silver chloride ratio. These particles are held in a polymeric binder support. The electrode formed from this material acts as a standard silver chloride reference electrode for the reaction.

Figure 1:
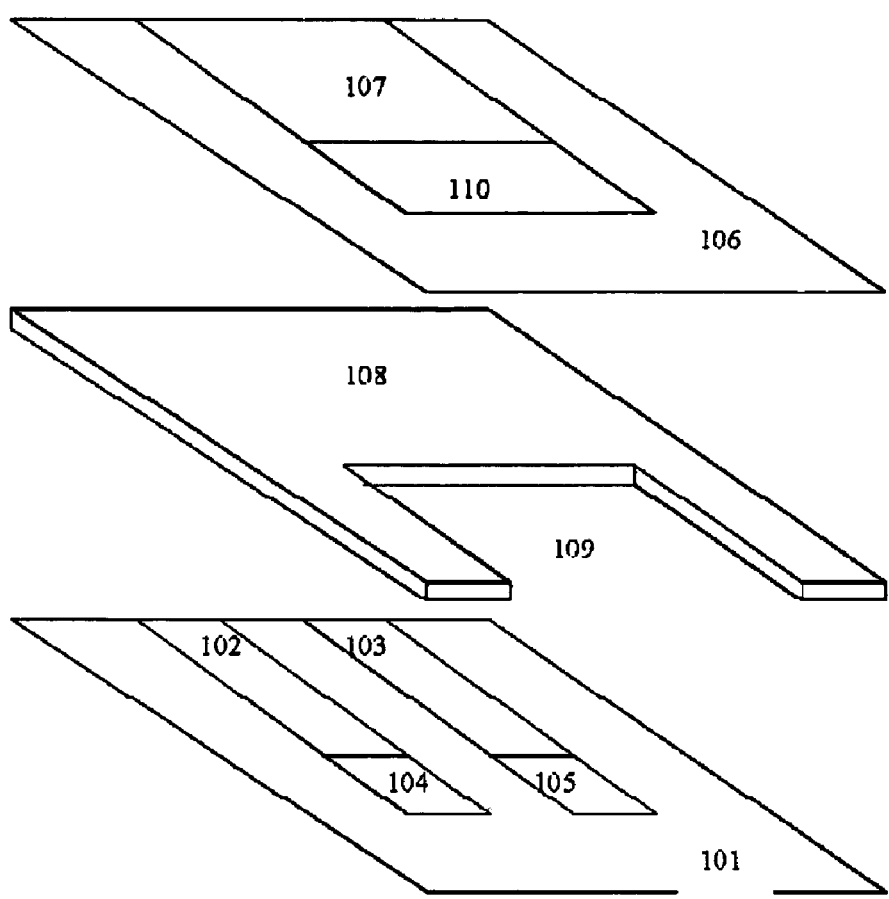
FIG. 1 shows a "sandwich" combined dry reagent electrochemical biosensor with glucose and beta-hydroxybutyrate electrodes on one surface, a chamber open on one end for receiving blood, and a reference electrode on a second surface.

A diagram of a "sandwich" type prototype sensor is shown in FIG. 1.

The prototype sensor may be produced by multiple screen-printing steps. Here the two working electrodes (102 and 103) are put on the same flat sheet of PVC (101), and the reference electrode (107) printed on a second sheet of PVC (106), and then laminated on top of the fist PVC sheet with spacer (108) to form a sandwich structure with an opening to admit blood (109).

The PVC sheet (101) holding the glucose and beta-hydroxybutyrate working electrodes may be prepared as follows: in the first printing step, the traces (102, 103) connecting the electrode areas to the external electrical connection means may be printed. In the second step, the NADH electrode (104) can be printed. In the third step, the H2O2 electrode (105) is printed. In the fourth step, the NADH electrode (104) is overprinted with buffered saline solution containing 30 U/Ml D3-Hydroxybutyrate dehydrogenase, 10 mM NAD. In the fifth step, the H2O2 electrode (105) is overprinted with a buffered saline solution containing 10,000 U/ml of aqueous *Aspergillus niger* glucose oxidase. Each working electrode is 1 mm wide, and the two electrodes are separated by a gap of 1 mm. After each printing step, the electrodes should be dried In a convection oven at 65.degree. C. for 30 minutes and then stored in a cool, dry, environment until the next printing step.

The PVC sheet holding the reference electrode may be produced in two screen-printing steps. In the first printing step, the traces connecting the electrode areas to the external electrical connection means are printed (107). In the second step, the reference electrode silver-silver chloride electrode (110) is made by screen printing Gwent product C61003D7 onto 20 mil thick PVC substrate using 156 mesh polyester screen. The electrodes are then dried in a convection oven at 65.degree. C. for 30 minutes and stored in a cool dry environment until used. The reference electrode may be 3 mm wide.

The two PVC layers should then be laminated together with an additional 10 mil (0.254 mm) thick spacer layer to result in a sandwich electrode with 3 mm.times.3 mm sized electrode surface area, and an internal volume of about 2.2 ul. This is shown in FIG. 1. Note that the electrodes on surfaces 106 and 101 all face the interior of the cavity.

Electrochemical sensing: To detect electrochemical activity, the electrodes should be connected to a circuit that challenges the electrode with a series of linearly variant patterns of potential versus time sweeps (Cunningham, "Introduction to Biolanalytical Sensors", Wiley Interscience, 1998 p 207–259). The output detected by this circuit may be interfaced with a Keithley KPCMCIA-16A1-C analog input PCMCIA card. This card, in turn, may be attached to a PC compatible notebook computer running Windows ME.

The software running the analog input card can acquire reaction data, display the data on the computer screen, and also store it in a file format suitable for later spreadsheet analysis. The glucose data (difference between the glucose electrode and the reference electrode) can be reported on one channel, and the beta-hydroxybutyrate data (difference between the beta-hydroxybutyrate electrode and the reference electrode) can be reported on a second channel. A third channel can monitor the differences between the glucose electrode and the beta-hydroxybutyrate electrode).

The digital output from the KPCMCIA board may be used to switch the analog electronics between sampling modes. At test beginning, the electronics can be set to resistance measurement mode. Here, the resistance between the glucose, b-hydroxybutyrate, and reference electrodes is monitored by a low voltage-low-current electrical "probe" signal every 100 milliseconds. Test onset is determined as the time when the resistance between all three electrodes was lowered. An error condition is set if the resistance between two of the electrodes dropped and resistance to the third electrode does not drop within about 1 second after the first drop.

Upon detection of resistance drop, the KPCMCIA board can be programmed to have its digital output signal switch the analog electronics to voltage/current measurement mode. The reaction data can then be taken and recorded.

The electrodes can be challenged with spiked whole blood (approximately 45 hematocrit) containing 100 mM glucose, 0 mM beta-hydroxybutyrate, 300 mM glucose 0 mM, beta-hydroxybutyrate, 100 mM glucose 2 mM beta-hydroxybutyrate, and 300 mM glucose, 2 mM beta-hydroxybutyrate. Each sample will produce a unique electrochemical reaction profile should be easily distinguished from the other sample types. The third channel, monitoring differential electrical current movement between the glucose electrode and the beta-hydroxybutyrate electrode, should give useful information to aid in removing the mild cross talk that occurs between the two electrodes at extreme glucose or beta-hydroxybutyrate levels.

Many other electrode chemistries and production methods are possible. As an example of one alternative, electrodes can be produced in general accordance with the sol-gel graphite composite technology as taught by U.S. Pat. No. 6,231,920.

In this alternative chemical embodiment, mixtures of surfactant stock solutions, and different graphite powders, each powder containing different types of various types or levels of enzyme and electron transport mediators, may be made up.

Surfactant stock solutions can be composed of: Aerosol OT (Fluka), Tetramethyl orthosilicate (Aldrich), and ultra-purified reagent grade water mixed in a 1:50:200 molar ratio and stirred until the solution clears.

Modified graphite powders can be made as follows:

Graphite powder intended for glucose sensors: Ferrocine (Alfa chemicals) may be dissolved in ethanol to produce a 2.5% Ferrocine/ethanol solution. This may then be added to Grade 38 graphite powder (Fisher Scientific) and mixed. The mix may then be put into open watch glasses and the ethanol allowed to completely evaporate in a low temperature (50° C.) convection oven. When the graphite-ferrocine mix is completely dry, this may then be mixed with a 5% aqueous *Aspergillus niger* glucose oxidase suspension (approximately 10,000 units per ml). This mix may again be put into open watch glasses and allowed to completely dry at room temperature.

Graphite powder intended for beta-hydroxybutyrate sensors: These electrodes were based upon a modification of the 3-hydroxybutyrate dehydrogenase, NAD, 4-methyl-o-quinone electrochemistry as taught by Batchelor et. al., (Analytica Chimica Acta 221 (1989), 289–294). To do this, 4-methyl-o-quinone is obtained (or synthesized according to the methods of Carlson and Miller (J. Am. Chem. Soc. 107 (1985), 479–485)). This may be dissolved in ethanol to produce a 1% 4-methyl-o-quinone solution. This may then be added to grade 38 graphite powder and mixed. The mixture may then be put into open watch glasses and the ethanol allowed to evaporate in a low temperature (50° C.) convection oven. When the graphite—4-methyl-o-quinone mixture is completely dry, this may then be mixed with an aqueous 10 mg/ml (30 units/ml) solution of D-3Hydroxybutyrate dehydrogenase (Roche molecular chemicals) that has been previously dialyzed against a buffered solution containing 20 mM NAD+ (Sigma) to remove the ammonium sulfate present in the commercial enzyme preparation, and to raise the NAD+ concentration in the final aqueous phase to 20 mM. The graphite-enzyme-NAD mix may then be put into open watch glasses and the water allowed to evaporate in a low temperature 50° C. convection oven.

At the time of electrode printing, 1 ml of the surfactant solution is mixed with 0.6 grams of the modified graphite powder, and the resulting paste screen-printed.

Coating electrodes with an inert hydrophilic, microporus layer: In order to help exclude as many interferents from the working area of the electrodes as possible, it is often advantageous to employ various microfiltration schemes to exclude red cells and other interferents. This may be done by a variety of means. The electrodes themselves may be designed to be microporous, as is taught by U.S. Pat. No. 6,231,920. Alternatively, or in combination, the electrode assembly may be covered with a microporous electrically inert material designed to admit sample while excluding as many interferents as possible. Such layers may be composed of previously synthesized filter materials, or built-up de-nouveaux on the test strip by means of self self-assembling chemical compositions, such as the mixed hydrophobic-hydrophilic particle techniques taught by U.S. Pat. Nos. 5,708,247 and 5,951,836.

There are a number of ways to induce micropores and microchannels into covering layers. In addition to the hydrophobic/hydrophilic techniques taught by U.S. Pat. Nos. 5,708,247 and 5,951,836, microchannels may be induced by a variety of alternative methods. For example, coatings consisting of all hydrophilic microparticles, and a binder, may be induced to form microchannels by alternate processing techniques, such as freeze drying, which tends to open up many micropores in a substrate as the ice slowly sublimates from a solid to gaseous phase. If the higher expense of freeze-drying is not desired, then the particles may be mixed with chemical agents that facilitate pore formation. Such agents include the addition of wax micro dispersions into the coating mix, followed by an organic solvent wash.

If the material is made up of particles with a defined spherical size, then pore formation is inevitable due to the natural pore structures obtained whenever spheres are closely packed. Microparticles suitable for this include the micron sized hydrophilic ropaque series of acrylic microspheres (Rohm and Haas corporation, PA). Here the size of the spherical particles is important, as too large a diameter will allow interfering substances in, while too small a diameter will impede fluid flow. Generally spherical particles in the 50 to 0.1 micron range, and preferably in the 10 to 0.5 micron range, are favored.

Binders include organic polymers such as hydroxyethylcellulose and the like. Such polymers are selected as to be electrically inert, hydrophilic, and capable of maintaining their structural integrity over the time course of the electrochemical reaction.

As previously discussed, it is often advantageous to cap electrodes with such electrically inert microporus structures to reduce interference. Alternatively, such electrically inert microporous structures may be employed as "spacer" layers between stacked arrays of active electrodes, as is discussed in example 2.

EXAMPLE 2

Multi-layer Combined Glucose, Beta-hydroxybutyrate Sensor

In an alternative embodiment, a porous spacer layer may be coated on top of the two sensor electrodes, and the reference electrode in turn coated on top of the spacer layer. Because the reference electrode is now elevated a significant distance above the primary support, an elevated stage with a secondary-conducting path may be added. Here a drop of blood is added directly to the primary support.

Figure 2:
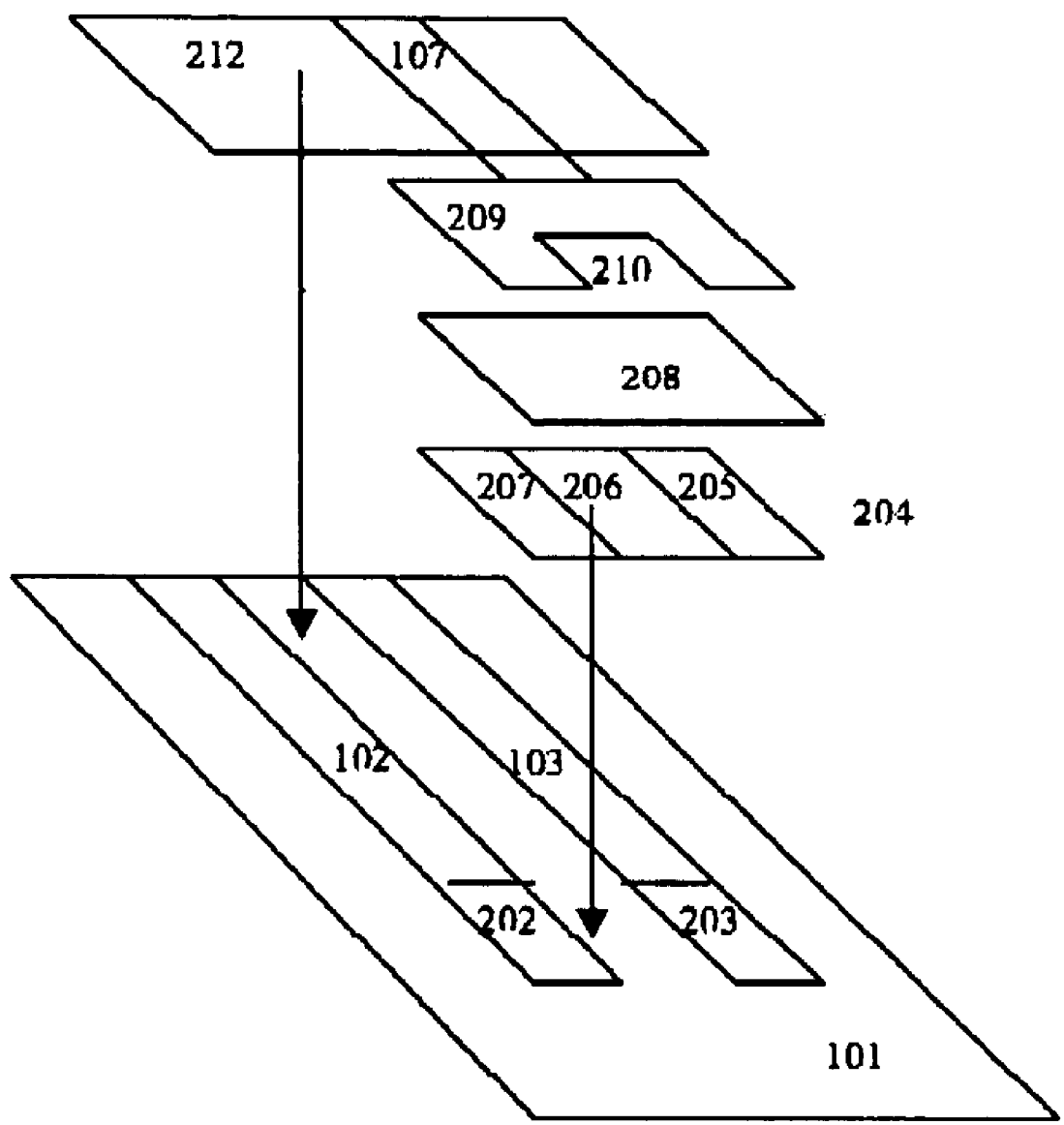
FIG. 2 shows a flat combined electrochemical dry reagent biosensor with glucose and beta-hydroxybutyrate electrodes on one surface, and a reference electrode located above the surface.

This "flat" reagent has its own unique set of advantages. Its more open design facilitates manufacturing. Additionally, some users may prefer applying sample to the more open reagent area. This scheme is shown in FIG. 2. In this scheme, conducting electrical paths (102, 103) are laid down on support (101) followed by the glucose and beta-hyroxybutyrate electrodes (202, 203). Usually this is done by a screen-printing process. In subsequent screen-printing processes, porous spacer layer (204) is printed to help fluid flow. Glucose and beta-hydroxybutyrate reagents (205 207) are printed on top of the porous spacer layer and are absorbed into the layer. A second porous spacer layer (208) is then printed. An elevated stage (212) to carry the reference electrode signal to the meter may then be added, either by lamination or thick film printing. Finally, reference electrode (209) and reference electrode conductive paths (107) are printed. This reference electrode may contain one or more open regions (210) to allow the applied sample to flow to the lower layers. In some embodiments, it may be advantageous to apply a final porous layer on top of reference electrode (209) to stabilize the electrode stack, and reduce imprecision due to hematocrit effects or other interferents.

In operation, a drop of blood is placed on top of reference electrode (209). The blood flows though electrode gap (210) into porous spreading layer (208). The blood then flows into porous electrodes (207) and (205). Electrical signals from glucose and beta-hydroxybutyrate production (202, 203) are conducted to the meter through electrical paths (102, 103). The reference electrode signal is conducted to the meter though elevated electrical path (107) on an optional different surface (212) elevated above first surface (101).

Although electrochemical based glucose tests are rapidly becoming the preferred modality for this type of reagent, it is also possible to create simple, easy to use, one blood drop activated optical glucose, beta-hydroxybutyrate reagents as well. This is shown in example 3

EXAMPLE 3

Optical Combined Glucose/beta-hydroxybutyrate Test Strip

In this example, a blood separating membrane, such as the membranes produced using the highly asymmetric membrane technology of the Filterite division of US Filtrations and Separations ("asymmetric polysulfone membranes", see U.S. Pat. Nos. 4,774,192 and 5,968,836) may be used to conduct the basic reaction. Typically filter membranes rated between 0.8 and 0.2 microns are preferred for this purpose. Asymmetric polysulfone membranes, used in this example, have a variable porosity structure with a large pore side on one side of the membrane, where sample is typically applied, and a small pore side, where the reaction results are typically observed.

Red cells in the blood sample applied to the large pore side migrate only partially into the membrane matrix, where they become trapped. By contrast, the plasma portion of the blood is free to move all the way to the small pore side. The membrane has sufficient optical opacity that if whole blood is applied to the large pore side of the membrane, only clear plasma is observed on the small pore side. Thus the color and reaction obscuring properties of the red cell hemoglobin are removed from the reaction. By embedding the appropriate reaction chemistry into the membrane, various types of chemical analytes can be observed, in particular, glucose and beta-hydroxybutyrate.

The small pore side of the membrane can be left open to the air. Alternatively, the small pore side may be covered with a transparent layer. Such transparent coverings may be desirable to improve reaction uniformity, resistance to environmental variables, and to reduce the chance of plasma from the sample contaminating the underlying meter. Such transparent membranes can reduce oxygen flow to the reaction however. Although this is not a problem for non-oxygen dependent enzymatic reactions, such as the beta-hydroxybutyrate reaction, it can be a problem if the commonly used glucose oxidase reaction for detecting glucose is used. Such glucose detection reactions are oxygen dependent, and thus might function sub optimally if the reaction matrix has a transparent layer that does not conduct oxygen well.

In this situation, use of the hexokinase glucose (glucose dehydrogenase) detection chemistry may be favored, since such reactions are not oxygen dependent. Additionally, such reactions use a number of the same reaction intermediates (NAD—NADH) and enzymatic reaction facilitators (diaphorase) etc., as the beta-hydroxybutyrate reaction. This may simplify test reagent construction, since the base membrane may be coated with reaction chemistry common to both enzymatic reactions, and the chemistry specific to each particular reaction may be then applied or streaked on in subsequent steps.

In order to work with a single 1–10 ul sized drop of blood, both the glucose and beta-hydroxybutyrate reaction zones should be situated close to each other. As an example, membrane in the reaction zone may be coated with the glucose specific chemistry on one half, and the beta-hydroxybutyrate chemistry on the other half. The two half sides may be separated by a gap, or by a semi-permeable "speed bump" zone. Alternatively, the membrane may be intermittently sealed in a dotted line fashion between the two sides, so that cross-diffusion between sides is reduced, yet the two areas still remain in fluid communication.

Since beta-hydroxybutyrate reagents will tend to be expensive, in an alternative configuration, it may be preferable to spot a smaller "dot" or "stripe" of the beta-hydroxybutyrate reagent onto a membrane otherwise nearly 100% saturated with the glucose reagent. In this case, the beta-hydroxybutyrate chemistry should be selected as to be resistant to the distortions caused by the large amount of neighboring glucose detection chemistry. This may be accomplished by a variety of means, such as incorporating hydrogen peroxide absorbing or inactivating chemistry in the beta-hydroxybutyrate reagent. In this case, the user will either be expected to judge the color of the dot or stripe by eye, or alternatively the meter may contain means, such as a linear photodetector array, etc., to image the spot or stripe, and calculate and report a separate measurement.

In yet another alternative embodiment, the two regents may be applied to the surface of neighboring optical fibers, one reagent per optical fiber. A holder that exposes both fibers to the same drop of blood may hold these fibers together. In this case, the meter will contain means to independently interrogate the two optical fibers, and report separate measurements.

In order to help visually distinguish this combined analyte test strip from the more commonly used single analyte test strip, it may be advantageous to include a tracking dye with either the glucose specific or beta-hydroxybutyrate specific second coating. A user could then use the colored stripe to help visually distinguish the combined test strip from the single analyte test strip.

In order that the tracking dye not interfere with subsequent colorimetric analysis of the reaction (either visual or photometric), it would be further advantageous if the dye rapidly undergo a transition from colored to uncolored (or alternate color) soon after sample application. Any dye that does not otherwise interfere with the reaction chemistry may be used here. As one example, the pH tracking dyes methyl red or phenol red may be applied to the surface of the membrane in a thin layer at pH that is mildly acidic relative to the rest of the reagent membrane. This thin layer is rapidly air dried immediately after application to keep the tracking dye distinct from the rest of the reagent in the membrane.

Under mildly acidic conditions, suitable pH tracking dyes absorb intensely around 520–550 nm and appear yellow. Upon application of sample, the dyes will mix with the more alkaline conditions in the applied sample and dried buffer from the rest of the membrane reagent, transition to a less acidic environment, and change their spectral properties. In particular, the dyes intense absorbance at 520–550 nm will stop (and thus the observed reflectance in the spectral region between 500–580 nm will increase), and instead the dyes will absorb at around 435 nm, and appear red. One advantage of this spectral response is that many indicator dyes useful for glucose and beta-hydroxybutyrate reactions have absorbance maximums that extend well into the 600 nm region, and thus there will be no additional cross-talk with the less acidic form of the pH indicator dyes. Many other dye reactions are possible and suitable, however.

A further advantage of such a tracking dye that undergoes a colored to clear transition upon hydration is that it can be used to help insure correct registration and tracking in an automated meter reader system. A frequent problem with such tests is that if a test strip reagent is not fully inserted (for example is only inserted so that half of the reaction zone is visible to the photo-optical reader), and then triggered by a optical reflectance drop (such as taught by U.S. Pat. Nos. 5,049,487; 5,843,692 and 6,268,162), then there is a significant possibility that the reaction would proceed with the meter reading only part of the colorimetric indicator. This could result in a potentially serious measurement error.

A meter designed to read a visually based combined functional glucose-beta-hydroxybutyrate test strip will normally have two photodetector systems, one designed to read the glucose portion, and the other designed to read the beta-hydroxybutyrate portion.

The asymmetric polysulfone membranes used in the examples here differ from the nylon membranes previously employed in the reflectance drop triggering methods of U.S. Pat. Nos. 5,049,487 and 5,843,692. Typically the color drop upon the placement of blood on an asymmetric polysuflone membrane is considerably less than the color drop upon the placement of blood on a nylon membrane. This is because the red-cell lytic nature of nylon membranes causes hemoglobin to rapidly transfer to the observation side of the nylon membrane. By contrast, non red cell lytic membranes, such as asymmetric polysuflone membranes, conduct relatively small amounts of hemoglobin to the observation side of the membrane. Thus use of reflectance drop techniques to detect sample application is relatively problematic when using reagents employing non-red cell lytic membranes are used.

By contrast, use of the color change of a tracking dye, induced by sample induced membrane hydration, has a number of advantages for test triggering purposes. Here, the test reagent is optimally designed so that the test strip must be fully inserted in order to bring the tracking dye portion of the membrane into full view. The meter can then be programmed to repeatedly interrogate the reflectance of the tracking dye portion of the membrane. Upon addition of sample, the tracking dye will then transition from a colored state to a non-colored state (or alternate color state), and the increase in reflectance at one or more wavelengths can then be used to trigger the start of the reaction. If the test strip is not fully inserted, or if the wrong type of test strip is used, the device will not trigger. This provides extra protection against user errors.

Modern blood glucose meters are extremely fast, and to be competitive, a dual-purpose glucose—beta-hydroxybutyrate reagent/meter system must also be as fast as possible. Here the reaction chemistry imposes some constraints, however. A sample with a high level of glucose or beta-hydroxybutyrate will typically take longer to complete than a reaction with a low level of these analytes. By necessity, an instrumented test that waits a fixed amount of time after reaction initiation in order to be sure to properly measure a sample containing a higher level of analytes will proceed with sub-optimal time efficiency with samples containing a lower level of analytes. In order to be as fast as possible, therefore, it is further advantageous to photometrically sample the reagent multiple times during the reaction, make real-time assessments as to if the reaction is heading to completion, and terminate the variable length test as soon as feasible.

Figure 3:
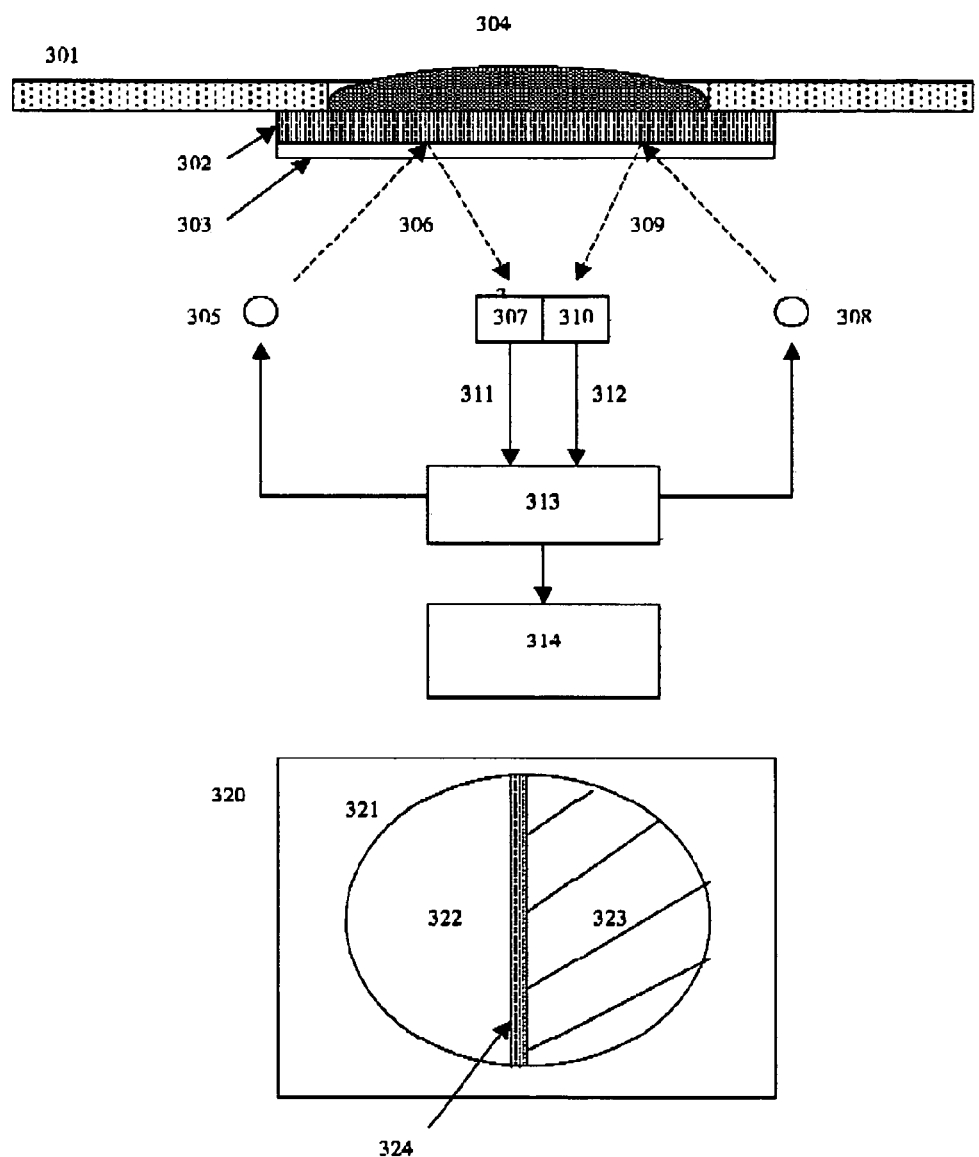
FIG. 3 shows a combined optical analyte dry reagent test strip/meter system. The test strip contains a single blood separating membrane, with regions striped with glucose detection reagents on one track, and beta-hydroxybutyrate detection reagents on the other track.

FIG. 3 shows an exemplary combined optical glucose, beta-hydroxybutyrate sensor. A plastic support (301) with a center aperture carries membrane (302), which may be covered by optional transparent layer (303). In this example, both the glucose and the beta-hydroxybutyrate reaction use dehydrogenase enzymes.

Label 20 shows a view from the top of plastic support (301) looking down on membrane (302) from above. Center aperture (321) can be seen. Membrane (302) has typically been first coated throughout with a reaction solution typically containing a buffer, reaction cofactors such as NAD and diaphorase enzyme, and typically one or more polymers and non-glucose sugars to stabilize the reaction components, and help modulate fluid flow. Membrane (302) will also contain two tracks. These tracks are usually produced by a second overcoating step using a thin layer of overcoat reagent solution followed by rapid drying.

One track (322) will contain the complementary enzyme for one of the two test reactions, such as hexokinase glucose, an indicator dye, and other reaction cofactors. A second track will contain die complementary enzyme for the other test reaction, such as beta-hydroxybutyrate dehydrogenase and other reaction cofactors. A second reagent indicator dye, (ideally with a different spectral response from the first indicator dye to minimize cross talk), will also be included. The second reagent track will usually be separated by gap (324) from the first reagent track.

Often, it may also be advantageous to include a moisture sensitive tacking dye (shown as the crosshatched area in (323)) that changes color from dark to light upon the addition of sample, into one or more of the two reagent tracks.

In operation. 1–10 or 1–20 microliters of whole blood (304) is applied to the sample-receiving (open pore in the case of asymmetric polysulfone) surface of membrane (302). Red cells and plasma are separated and plasma flows through to die optical reading sick, which may be covered by optional transparent membrane (303). The reaction zones (322) and (323) become hydrated with sample.

While this is going on, die underside of the test strip is being observed by a microprocessor controlled optical stage underneath the membrane (305–312). In operation, the optical stage periodically polls the state of tracking dye-coated membrane (323). This is done by a light source (308), controlled by microprocessor (313). This light illuminates the underside of the test strip (302, 303) and is detected by a microprocessor-controlled photodetector (310).

Typically light sources (305) and (308) will be provided by light emitting diodes (LEDs), and have defined spectral characteristics. In particular, light source (308) will optimally have spectral characteristics optimized to be sensitive to the color transition of the tracking dye, and also sensitive to die color transition of die indicator dye. If one LED does not have the required wavelength spectral properties for both purposes, two LEDs (or other light sources) with different spectral properties may be used in (308).

Upon sample addition, tracking dye (323) alters its spectral state and the increase in reflectance on at least one wavelength is detected by photodetector (310). This initiates test timing. Both reaction zone areas (322) and (323) are observed periodically by light source (305) and photodetector (307) (for zone (322)) and by light source (308) and photodetector (310) (for zone (323)). Note that depending upon the optical geometry, the same photodetector may be used for both (307) and (310).

The microprocessor (313) monitors the kinetics of both reactions. When it accumulates enough data points to either determine reaction rate, or extrapolate reaction endpoint levels, microprocessor (313) stops accumulating further data, calculates the final answer, and typically will display both answers on display (314).

EXAMPLE 4

Combined Electrochemical—Optical Sensor

In this example, a hybrid detector element is formed containing one detection element based upon electrochemical technology, and a second detection element is based upon optical technology.

Here, the electrochemical element may be a conventional electrochemical detector element, such the electrochemical glucose sensors discussed previously. The optical element may be a membrane based optical sensor, such as the optical membrane beta-hydroxybutyrate sensors discussed previously.

One advantage of electrochemical sensors, however, is that the sensor element only needs to be connected to a meter by an electrical contact. As a result, electrochemical sensor—meter systems can be designed in which the electrochemical detector protrudes a significant distance away from the main body of the meter. This improves the user interface, because a drop of blood can be more easily applied to the protruding sensor. Additionally, it is often easier to insert or remove sensors if they stick out from the main meter body.

By contrast, membrane based optical sensors typically need to be held closely to the optical portion of a meter. This makes sample application more difficult, as applied blood thus has a higher chance of smearing onto non-sensing regions of the meter body, creating an undesired mess.

To avoid these ergonomic issues, it may often be advantageous to use an optical conductive pathway, such as a molded optical wave guide, optical fiber or the like to transmit the optical signal from the second optical sensor to a detection device. The optical wave-guide carries the optic signal along the same pathway used to conduct the electrical signals. Because the optical reagents need be applied only to the tip of the optical wave-guide probe, only extremely small amounts of reagent and blood are needed for the reaction. As a result, an optical sensor may be added to an electrochemical sensor with only minimal perturbation to the design of the electrochemical sensor.

Figure 4:
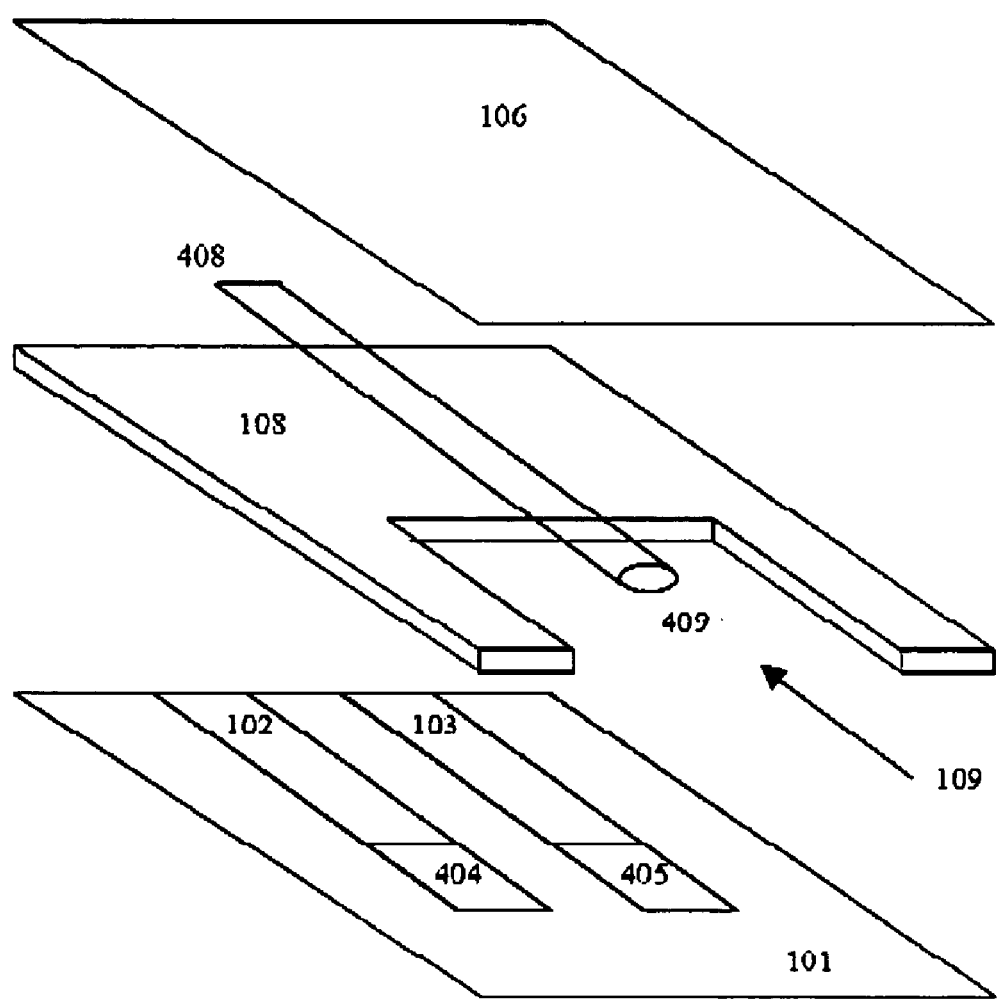
FIG. 4 shows a dual mode optical-electrochemical sensor. This test strip consists of an electrochemical glucose sensor, and a fiber optic beta-hydroxybutyrate sensor, mounted so that the same drop of blood activates both sensors.

A diagram showing this combined electrochemical optical sensor is shown in FIG. 4. Here, the substrate (101) contains electrodes (102, 403) making contact with conventional glucose electrochemical reagents (404, 405). This, in turn, is separated by a spacer layer (108) from second substrate (106). In practice, first substrate (101), spacer (108), and second substrate (106) are combined to form a single unit, containing a chamber (109), which is used to receive the blood sample. The unit additionally contains an optical wave-guide element (408) placed between substrate (101) and (106). This optical wave-guide is tipped with a colorimetric, fluorescent, or luminescent reagent (409), such that the analyte in the blood admitted to reaction chamber (109) produces a detectible optical signal, which is transmitted to an optical detection apparatus or meter by way of optical wave guide (408).

The configuration of optical wave guide (408) may be optimized for the specifics of the meter design and reaction chemistry. In some embodiments, it may be desirable to utilize an asymmetric design in which the meter side of the optical wave-guide is larger than the sample side of the optical wave-guide. This will facilitate optical coupling between the meter's optical excitation source and detector, and the wave-guide. At the same time, the sample side of the wave-guide can be kept extremely small, which minimizes the amounts of reagents and blood needed for the test.

Reagents will typically be applied to the sensor end of the optical wave-guide with appropriate particulate or polymeric agents so as to create a relatively tough, but fluid permeable, cap on the tip of the wave-guide. Reaction chemistry indicator dyes and detection wavelengths will typically be chosen to give optimal signal-to-noise ratios with whole-blood samples. This favors the use of indicator dyes and detection wavelengths operating in the red and infrared end of the spectrum (600 nm or greater), where interference from the hemoglobin present in whole blood is relatively minimal.

For calorimetric detection chemistries, it may often be advantageous to use multiple wavelength detection means employing both an indicator dye detection wavelength, and a reference wavelength where the indicator dye does not absorb as strongly. In this way, distortion of the colorimetric signal due to varying levels of hemoglobin or other interfereants in the sample may be minimized.

The configuration of the optical wave-guide may also be optimized for the problem at hand. As an example, in some situations, it may be advantageous to employ a dual chamber optical wave-guide with separate or partially separate optical conduits for the excitation signal and return signal.

For configurations employing single-fiber optical wave guides (fiber optics), use of fluorescent indicator dyes has certain advantages. The excitation wavelength, and the return fluorescent wavelength from the indicator dye, may travel through the same optical fiber with minimal confusion or cross-talk. Due to the extreme cost sensitivity of high volume mass-market glucose test strips, simple designs such as this are helpful. Simple reagent designs, which use minimal amounts of optical materials or reagents, have inherently lower production costs.

In the single fiber configuration, the reagent test-strip itself is kept extremely simple to reduce costs. Here, the single optical fiber is plugged into the optical unit of a meter, and any additional optical processing, beam splitting, and the like is performed by the meter's optical sensor unit. Ideally, to reduce costs to a minimum, the meter's optical sensor device is a miniaturized integrated optical chip, such as a MEMS optical chip.

In operation, sample is applied to reaction chamber (109). This sample interacts with the electrochemical sensor, producing a change in die electrical characteristics of the electrodes, such as an amperometric, potentiometric, conductometric, impedance, or other electrically detectible change, that signals the start of the test.

The meter will contain both electrical means to monitor the electrochemical reaction, and optical means to monitor the optical reaction. The meter monitors the reaction progress of the electrochemical reaction through electrical contact with electrodes (102, 103). The meter uses die same electrical signal used to trigger the start of the electrochemical reaction to begin monitoring the optical reaction through optical contact with optical wave guide (408).

Usually, the electrochemical reaction will proceed faster than the optical reaction. The meter may be programmed to immediately report the electrochemical reaction, and additionally may be programmed to either always display the optical reaction, or alternatively only display the optical reaction if the results of the electrochemical reaction suggest that the optical reaction results may be medically relevant.

As an example, the meter may be programmed to immediately report glucose, and not indicate that a second beta-hydroxybutyrate reaction is proceeding, unless the glucose results fall into a high range where ketoacidosis is a genuine possibility. However if the glucose level falls into a range where ketoacidosis is a potential concern, the meter may display an alternative message such as "Wait—checking ketones" while the ketone test automatically continues. In this way, the test may proceed with optimum speed most of the time, while still providing a valuable emergency ketoacidosis warning.

Note that although FIG. 4 shows a fiber optical wave guide operating in conjunction with an electrochemical sensor where both electrodes are on the same solid support, it should be obvious that these concepts will apply equally well to other electrode configurations as well. As an example, each electrode could be mounted on a different support surface, such as surfaces (101) and (106). Alternatively, electrode configurations as shown in FIG. 2 may be used.

Figure 5:
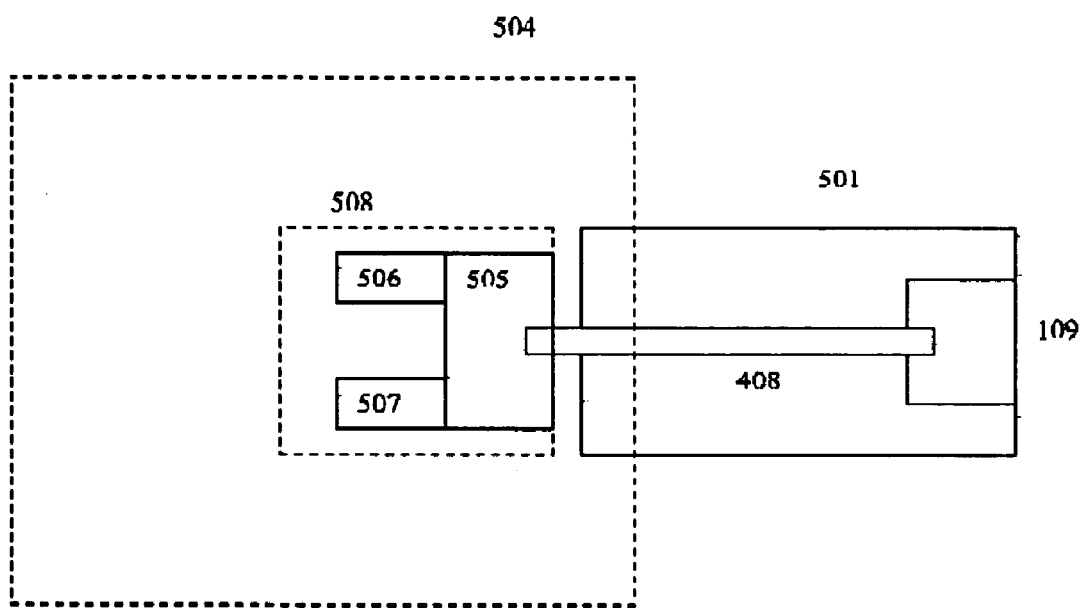
FIG. 5 shows a detail of the docking and optical interface between a dual mode optical—electrochemical sensor, and a meter. Here, the optical sensor consists of a single strand of optical fiber, capped with reagent.

FIG. 5 shows a close up of the interface between a test strip (501) containing an opening to admit a sample (109), a single fiber optic sensor (409); docking to meter (504). This test strip may additionally contain electrochemical sensor electrodes (not shown) that also make contact with meter (504).

In this scheme, optical fiber (408) docks with an optical adapter element (505), which further may split the optical signal between a wavelength emitter element (506) and a detector element (507). Ideally, to reduce manufacturing costs, two or more of these detector elements and or adapter unit (505) are integrated onto a single custom optical chip (508). The information from the optical detector, and the electrochemical detectors, is then processed by a microprocessor, converted to a clinically useful set of values, and communicated to the user.

What is claimed is:

1. A dry reagent diagnostic device for the simultaneous enzymatic analysis of two different analytes in a single application of a single 1–20 ul sample of whole blood, wherein
    the fast analyte is determined by a fast reaction zone, and a second reaction zone, physically separated from the first reaction zone, determines the second analyte;
    a fluid bridge formed by the applied sample connects the two reaction zones;
    said first reaction zone and second reaction zone having reaction materials and geometry; selected to allow simultaneous rehydration and activation of both zones by a single unseparated whole blood drop;

said reaction zone materials and geometry being selected so as to return detectable analyte signals in the presence of whole blood;

said reaction zone materials and geometry being selected as to generate a detectable sample application signal upon initial contact with whole blood;

said detectable sample application signal being capable of triggering an automated reaction zone reader which is capable of performing subsequent test timing in an automated manner;

and at least one of the reaction zones produces a detectable change in an optical signal.

2. The device of claim 1, in which the analytes are glucose and beta-hydroxybutyrate.

3. The device of claim 2, in which one reaction zone is an electrochemical reaction zone, and the reaction detected is an electrochemical reaction, wherein said device has at least one working electrode for said electrochemical reaction zone, and at least one reference electrode.

4. The device of claim 3, in which said at least one electrode contains carbon particles.

5. The device of claim 3, in which said electrochemical reaction zone detects glucose, said electrochemical reaction zone contains a glucose sensing electrode, and said glucose electrode contains or is associated with a glucose oxidase enzyme and an electron transfer mediator.

6. The device of claim 3, in which said electrochemical reaction zone detects glucose, said electrochemical reaction zone contains a glucose sensing electrode, and said glucose electrode contains or is associated with glucose dehydrogenase enzyme and an electron transfer mediator.

7. The device of claim 3, in which said electrochemical reaction zone detects beta-hydrozybutyrate, said electrochemical reaction zone contains a beta-hydroxybutyrate sensing electrode, and said beta-hydroxybutyrate electrode contains or is associated with beta-hydroxybutyrate dehydrogenase enzyme and an electron transfer mediator.

8. The device of claim 3, in which one or more layers of a microporus, microparticle and binder composition, which allows plasma to pass but blocks red cells, cover said at least one working electrode for said electrochemical reaction zone.

9. The device of claim 8, in which one or more layers of the microporus, microparticle and binder composition are rendered microporous through a freeze-drying step.

10. The device of claim 8, in which the microporous microparticle composition is composed of spherical particles with a diameter between 0.1 and 50 microns.

11. The device of claim 2, in which said optical signal is selected from group consisting of colorimetric, fluorescent, or luminescent signals.

12. The device of claim 11, in which said analyte determined by said reaction zone producing a detectable change in an optical signal is glucose and said reaction zone of the device contains or is associated with a glucose oxidase enzyme, peroxidase, and a hydrogen peroxide sensitive optical indicator dye.

13. The device of claim 11, in which said analyte determined by said reaction zone producing a detectable change in an optical signal is glucose and said reaction zone of the device contains or is associated with a glucose dehydrogenase enzyme, NAD, diaphorase, and a NADH sensitive optical indicator dye.

14. The device of claim 11, in which said analyte determined by said reaction zone producing a detectable change in an optical signal is beta-hydroxybutyrate and said reaction zone of the device contains or is associated with a beta-hydroxybutyrate dehydrogenase enzyme, NAD, diaphorase, and a NADH sensitive optical indicator dye.

15. The device of claim 1, in which a chemical sample application signal detection means is incorporated into at least one of the reaction zones, and in which the chemical sample application signal detection means changes its colorimetric, fluorescent, or luminescent state upon contact with the liquid sample.

16. The device of claim 15, in which an increase in reflectance on at least one wavelength of the chemical sample application signal detection means is used to trigger the start of an automated meter system that monitors the reaction optically.

17. The device of claim 1, in which the first analyte produces an electrochemical signal, and in which the second analyte produces a detectible change in an optical signal.

18. The device of claim 17, in which the device contains conducting electrodes to transmit the electrochemical signal, and an optical wave guide to transmit the optical signal.

19. The device of claim 18, in which the optical wave guide is a single optical fiber.

20. A method for determining the concentration of two or more analytes in a single sample of whole blood with a volume under 20 ul, comprising the steps of;

applying said blood sample to a dry reagent diagnostic device in a single application, said dry reagent diagnostic device containing at least two reaction zones;

wherein a first analyte in said sample is determined by a first reaction zone, and a second reaction zone, physically separated from the first reaction zone, determines a second analyte in said sample;

forming a fluid bridge with the applied blood sample to connect; all reaction zones on said device;

said first reaction zone and second reaction zone having reaction zone materials and geometry; and selected to allow simultaneous rehydration and activation of all zones by a single unseparated whole blood drop;

said reaction zone materials and geometry being selected as to return detectable analyte signals in the presence of whole blood;

and determining the concentration of at least one of said analytes from at least one of said reaction zones by a detectable change in an optical signal.

21. The method of claim 20, in which at least one analyte produces an electrochemical signal, and in which at least one analyte produces a detectible change in an optical signal.

22. The method of claim 20, in which the dry reagent diagnostic device contains conducting electrodes to transmit an analyte produced change in an electrochemical signal, and an optical wave guide to transmit an analyte produced change in an optical signal.

23. The method of claim 20, in which said reaction zone materials and geometry are selected as to generate a detectable sample application signal upon initial contact with whole blood; and said detectable sample application signal being capable of triggering an automated reaction zone reader which is capable of performing subsequent test timing in an automated manner.

* * * * *